United States Patent [19]

Smithers

[11] 4,112,120

[45] Sep. 5, 1978

[54] METHODS AND COMPOSITIONS FOR USE IN ANIMAL HUSBANDRY

[75] Inventor: Michael James Smithers, Macclesfield, England

[73] Assignee: Imperial Chemical Industries Limited, London, England

[21] Appl. No.: 667,440

[22] Filed: Mar. 16, 1976

[30] Foreign Application Priority Data

Apr. 17, 1975 [GB] United Kingdom ............... 15854/75

[51] Int. Cl.$^2$ ................... A61K 31/175; A61K 31/17; A61K 31/155; A61K 31/415

[52] U.S. Cl. ................................ 424/323; 424/273 R; 424/322; 424/326

[58] Field of Search ................ 424/323, 326, 273, 322

[56] References Cited

FOREIGN PATENT DOCUMENTS 774,794  5/1957  United Kingdom ..................... 424/323

OTHER PUBLICATIONS

*Feed Additive Compendium,* 1965, Miller Pub. Co., Minn., Minn., pp. 332–338.
*The Merck Veterinary Manual,* p. 1338, Merck & Co., Inc., Rahway, N. J. (1967).

Primary Examiner—Frederick E. Waddell
Attorney, Agent, or Firm—Cushman, Darby & Cushman

[57] ABSTRACT

The disclosure relates to method for use in the husbandry of meat-producing domestic animals which comprises the oral administration to the animals of a p-benzoquinonedi-imide derivative, or a dihydro derivative or a salt thereof, and to compositions suitable for direct feeding to animals, in the method of the invention, or suitable for dilution with an animal foodstuff to give a supplemented foodstuff suitable for direct feeding to animals in the method of the invention; also to certain of the p-benzoquinonedi-imide derivatives which are novel compounds, and a process for their manufacture.

3 Claims, No Drawings

METHODS AND COMPOSITIONS FOR USE IN ANIMAL HUSBANDRY

This invention relates to methods, compositions and chemical compounds for use in animal husbandry for improving the growth of animals and for improving the efficiency of the utilisation of animal foodstuffs.

According to the invention, there is provided a method for use in the practice of animal husbandry which comprises orally administering to meat-producing domestic animals, for example chickens, turkeys, ducks, geese, pigs, sheep, cattle or rabbits, a quinone derivative of the formula:

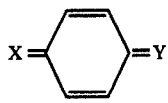

wherein X is a guanidinoimino radical, optionally bearing one to three substituents on nitrogen selected from $C_{1-3}$ alkyl radicals and phenyl radicals optionally substituted by halogen atoms, for example a chlorine atom; or a (1,3-diaza-2-ene-heterocyclic)-2-hydrazono radical; and Y is a guanidinoimino radical optionally substituted as defined above; a (3-nitroguanidino)imino radical; a semicarbazono or thiosemicarbazono radical optionally substituted on N-4 by a carbamoyl radical, a benzyl radical, a $C_{1-3}$ alkyl or alkenyl radical, or a phenyl radical; or a 3-[4-(guanidinoimino)cyclohexa-2,5-dienylideneimino]guanidinoimino or 3-(4-semicarbazonocyclohexa-2,5-dienylideneimino)guanidinoimino radical or a dihydro derivative thereof; or a salt thereof.

In the quinone derivative of the formula I, X or Y, when either is a guanidinoimino radical, is preferably unsubstituted or bears one substituent only on nitrogen, preferably on the terminal nitrogen, and the substituent is preferably a methyl, benzyl or carbamoyl radical. A suitable value for X when it is a (1,3-diaza-2-ene-heterocyclic)-2-hydrazono radical is, for example, a 2-imidazolin-2-ylhydrazono radical and a suitable optional substituent in Y when it is a semicarbazono or thiosemicarbazono radical is, for example, a methyl radical. A suitable dihydro derivative is one wherein the quinone ring has been reduced to an aromatic p-phenylene ring; and a suitable salt is, for example, a hydrochloride, nitrate, sulphate, hydrogen sulphate or toluene-p-sulphonate.

A preferred group of compounds which may be used in the method of the invention comprises quinone derivatives of the formula I wherein X is a guanidinoimino, (3-methylguanidino)imino or 2-imidazolin-2-ylhydrazono radical and Y is a guanidinoimino, (3-methylguanidino)imino, (3-nitroguanidino)imino, 3-(4-chlorophenyl)guanidinoimino, semicarbazono, 4-benzylsemicarbazono, 4-carbamoylsemicarbazono, thiosemicarbazono, 3-[4-(guanidinoimino)cyclohexa-2,5-dienylideneimino]guanidinoimino or 3-(4-semicarbazonocyclohexa-2,5-dienylideneimino)guanidinoimino radical; dihydro derivatives thereof wherein the quinone rings have been reduced to aromatic p-phenylene rings; and the hydrochloride, nitrate, sulphate,, hydrogen sulphate and toluene-p-sulphate salts thereof, or a similar salt of a dihydro derivative thereof as defined above.

Preferred quinone derivatives which may be used in the method of the invention are N-guanidino-N'-ureido-p-benzoquinonedi-imide, N-(3-methylguanidino)-N'-ureido-p-benzoquinonedi-imide, N-guanidino-N'-(4-methylsemicarbazono)-p-benzoquinonedi-imide, N-guanidino-N'-thioureido-p-benzoquinonedi-imide, N-guanidino-N'-(3-nitroguanidino)-p-benzoquinonedi-imide and the hydrochlorides thereof, and 1,3-bis[4-(guanidinoimino)cyclohexa-2,5-dienylideneimino]-guanidine and its trihydrate.

In the method of the invention, the quinone derivative or a dihydro derivative or salt thereof or a salt of a dihydro derivative thereof is preferably orally administered to the animals in their diet, that is to say in admixture with solid food, dissolved in the drinking water, or, for young animals such as pigs or calves, dissolved in skim milk. It is generally convenient to administer the quinone derivative or a dihydro derivative or salt thereof, or a salt of a dihydro derivative thereof mixed with the animals' normal nutritionally balanced diet, and such a supplemented foodstuff should contain from 0.0001% w/w (1g. per metric ton) to 0.025% w/w (250g. per metric ton) of a quinone derivative, or a dihydro derivative or salt thereof, or a salt of a dihydro derivative thereof as defined above, or from 0.0001% w/w (1g. per metric ton) to 0.005% w/w (50g. per metric ton) of a preferred compound. The animals may be fed with such a supplemented foodstuff for substantially the whole of their growing period, or for only a part of their growing period, preferably the early part and/or the period leading up to slaughter. The increase in growth rate achieved by the practice of the method of the invention enables animals to be brought to market weight, or slaughter weight, in a shorter growing period than normal, or it enables heavier animals to be produced at the end of the normal growing period. The practice of the method of the invention also achieves economic benefit for the farmer and the agricultural industry in that a given weight gain in the animals is achieved using less food than normal by reason of the increase in feed efficiency achieved by the method.

According to a further feature of the invention there is provided a composition for use in the method of the invention, which comprises a quinone derivative or a dihydro derivative or a salt thereof, or a salt of a dihydro derivative thereof as defined above, together with a liquid or solid, edible non-toxic diluent or carrier.

Suitable quinone derivatives, and dihydro derivatives and salts thereof and salt of dihydro derivatives thereof are those defined above.

A suitable liquid diluent or carrier is, for example, drinking water, whole milk or skim milk. A suitable solid, edible non-toxic diluent or carrier may be, for example, a nutritionally balanced animal foodstuff, for example a standard conventional broiler chicken diet of ground grain and grain by-products, animal protein supplemented by vitamins and minerals, a standard commercial pig fattening or finishing diet or other conventional animal foodstuff, or it may be an inert, solid diluent or carrier, for example kaolin, talc, calcium carbonate, fuller's earth, attapulgus clay, ground oyster shells, ground limestone, starch or lactose.

The composition of the invention may take the form of a supplemented foodstuff suitable for direct feeding to animals, in which case it will contain from 0.0001 to 0.025% w/w of a quinone derivative or a dihydro derivative or salt thereof, or a salt of a dihydro derivative thereof preferably 0.0001 to 0.005% w/w of a preferred compound, in admixture with a conventional animal foodstuff, or it may take the form of a concentrated premix for dilution with a conventional foodstuff to produce a supplemented foodstuff suitable for direct feeding, and such a premix will contain from 0.025 to 50% w/w of a quinone derivative, or a dihydro derivative or salt thereof, or a salt of a dihydro derivative thereof, in admixture with either a nutritionally balanced animal foodstuff or an inert solid diluent of no nutritional value, such as ground limestone. Such a premix may be diluted in conventional manner, preferably in two or more steps to ensure even mixing, with a conventional animal foodstuff to give a supplemented foodstuff suitable for direct feeding to animals in the method of the invention.

According to a further feature of the invention there is provided a process for the manufacture of a solid composition as defined above which comprises uniformly mixing a quinone derivative, or a dihydro derivative or salt thereof, or a salt of a dihydro derivative thereof, as defined above, with a solid, edible, non-toxic diluent or carrier.

According to a further feature of the invention there is provided a novel quinone derivative of the formula:

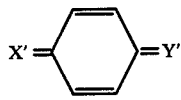
II wherein either X' is a guanidino radical and Y' is a 4-methylsemicarbazono, 4-benzylsemicarbazono, 4-carbamoylsemicarbazono, (3-methylguanidino)imino, (3-nitroguanidino)imino, 3-(4-chlorophenyl)-guanidinoimino or 3-[4-(guanidinoimino)cyclohexa-2,5-dienylideneimino]guanidinoimino radical, or X' is a (3-methylguanidino)imino, 2-imidazolin-2-ylhydrazono or 3-(4-semicarbazonocyclohexa-2,5-dienylideneimino)-guanidinoimino radical and Y' is a semicarbazono radical, or X' is a (3-methylguanidino)imino radical and Y' is a 4-methylsemicarbazono radical.

Preferred novel quinone derivatives of the invention are N-(3-methylguanidino)-N'-ureido-p-benzoquinonedi-imide, N-guanidino-N'-(4-methylsemicarbazono)-p-benzoquinonedi-imide and 1,3-bis[4-(guanidinoimino)cyclohexa-2,5-dienylidene-imino]-guanidine and salts thereof.

According to a further feature of the invention there is provided a process for the manufacture of a novel quinone derivative of the formula II as defined above, which comprises the reaction of a quinoneimide derivative of the formula:

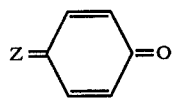
III wherein Z represents X' or Y' as defined above, with an amino compound of the formula Z'H, wherein Z' represents X' or Y', and wherein Z and Z' are different, or with a salt thereof, for example the hydrochloride or bicarbonate salt.

The invention is illustrated, but not limited, by the following Examples:

EXAMPLE 1

Premixes suitable for dilution with an animal foodstuff may be manufactured by incorporating 5, 10, 25, 50, or 100g. of N-guanidino-N'-ureido-p-benzoquinonedi-imide in a standard broiler chicken diet comprising ground maize and fishmeal, with added lysine, methionine, vitamins and minerals so that the final weight of the premix is 500g.

Other premixes may be manufactured similarly by replacing the N-guanidino-N'-ureido-p-benzoquinonedi-imide with a similar quantity of N-guanidino-N'-thioureido-p-benzoquinonedi-imide, N-guanidino-N'-(3-nitroguanidino)-p-benzoquinonedi-imide or N,N'-bis-guanidino-p-benzoquinonedi-imide, or with any other quinone derivative as hereinbefore described.

EXAMPLE 2

Premixes suitable for dilution with an animal foodstuff may be manufactured by the process described in Example 1, using ground limestone in place of the standard broiler chicken diet.

EXAMPLE 3

An animal foodstuff suitable for direct feeding to poultry may be manufactured by intimately mixing 500g. of a premix, obtained as described in Example 1 or 2, with 4.5 kg. of standard broiler chicken diet, and then uniformly mixing the mixture so obtained with 995 kg. of standard broiler chicken diet to obtain a poultry foodstuff containing 5, 10, 25, 50 or 100 g. of a quinone derivative per metric ton, depending on the concentration of quinone derivative in the premix used.

EXAMPLE 4

Groups of 20 randomised 1-day old chickens were placed in small floor pens, bedded with wood shavings and provided with automatic water fountains. The birds in 16 randomly chosen such pens were fed for 6 days on a nutritionally balanced control diet containing one known growth promoter, and the birds in other pens were fed for the same period on the same basal diet to which the indicated weight in parts per million of a quinone derivative was added. At the end of the test period, the birds were weighed, and the total liveweight for each pen was determined. In each test, pens of birds treated with the known growth promoters nitrovin (10 p.p.m.) and penicillin (25 p.p.m.) were included as positive controls. The following results were obtained for the compounds:

1. N-guanidino-N'-ureido-p-benzoquinonedi-imide hydrochloride.
2. N-guanidino-N'-thioureido-p-benzoquinonedi-imide.
3. N-guanidino-N'-(3-nitroguanidino)-p-benzoquinonedi-imide hydrochloride.
4. N,N'-bis-guanidino-p-benzoquinonedi-imide dinitrate.

The "weight difference" is the difference between the weight of a treated group (A) and the weight of an untreated control group (B) expressed as a percentage of the weight of the untreated control group, that is:

$$\frac{A - B}{B} \times 100$$

| | Weight Difference | | | | |
|---|---|---|---|---|---|
| Compound No. | 50 ppm. | 25 ppm. | 10 ppm. | Nitrovin 10 ppm. | Penicillin 25 ppm. |
| 1 | 24.9* | 21.3* | 7.1* | 13.9* | 12.3* |
| 2 | 19.5* | 9.4* | 4.5+ | 13.9* | 12.3* |
| 3 | 14.8* | 8.1* | 5.8+ | 13.9* | 12.3* |

-continued $$\frac{A-B}{B} \times 100$$

Weight Difference

| Compound No. | 50 ppm. | 25 ppm. | 10 ppm. | Nitrovin 10 ppm. | Penicillin 25 ppm. |
|---|---|---|---|---|---|
| 4 | 4.6+ | — | — | 13.9* | 12.3* |

*significantly different from untreated control at the p<0.001 level.
+significantly different from untreated control at the p<0.01 level.

EXAMPLE 5

In a similar test, N-guanidino-N'-thioureido-p-benzoquinonedi-imide was tested at different inclusion levels between 10 and 500 p.p.m. with the following results (expressed as in Example 4):

| Inclusion level (p.p.m.) | Weight difference |
|---|---|
| 500 | 24.1* |
| 250 | 24.1* |
| 100 | 22.4* |
| 50 | 16.8* |
| 25 | 7.8* |
| 10 | 1.6 |

*significantly different from untreated control at the p <0.001 level.

EXAMPLE 6

1-Day old cockerels were randomised and placed in groups of 30 in small floor pens, bedded with wood shavings and provided with automatic water fountains. The birds in 6 randomly chosen such pens were fed for 4 weeks on a nutritionally balanced control diet containing no known growth promoter. Other groups of six randomly chosen pens were fed the same diet to which had been added compounds under test at the indicated weight in parts per million. At the end of the test period the mean final liveweight of the birds in each group of six pens was recorded and the "feed conversion ratio" (kg. feed per kg. final liveweight) was calculated. The following results were obtained with nitrovin, a known growth promoter, N-guanidino-N'-thioureido-p-benzoquinonedi-imide and N-guanidino-N'-ureido-p-benzoquinonedi-imide hydrochloride at the dose levels indicated:

| Diet | | mean final liveweight (g) | "feed conversion ratio" |
|---|---|---|---|
| Basal | | 313.2 | 2.09 |
| Basal + nitrovin | 10 ppm. | 336.5* | 2.00* |
| Basal + N-guanidino-N'-thiourido-p-quinonedi-imide | 50 ppm. | 357.0*** | 1.96** |
| " | 25 ppm. | 349.5** | 2.00+ |
| " | 10 ppm. | 338.2** | 2.04 |
| Basal + N-guanidino-N'-ureido-p-benzoquinonedi-imide hydrochloride | 50 ppm. | 358.8*** | 1.94*** |
| " | 25 ppm. | 356.7*** | 1.95*** |
| " | 10 ppm. | 342.2** | 1.99* |

***Significantly different from control (basal) at p <0.001 level.
**Significantly different from control (basal) at p <0.01 level.
*Significantly different from control (basal) at p <0.05 level.
+Significantly different from control (basal) at p <0.10 level.

EXAMPLE 7

A mixture of N-guanidino-p-benzoquinonimide (8.2g.; 50 mmoles) and 1-amino-2-nitroguanidine (6.0g.; 50 mmoles) in N-hydrochloric acid (100ml.) was shaken automatically for 3 hours at room temperature. The solid product was collected, washed with water and dried in vacuo, to give N-guanidino-N'-(3-nitroguanidino)-p-benzoquinonedi-imide, m.p. 250° C. (with decomposition).

EXAMPLE 8

The procedure described in Example 4 was repeated, using different test compounds, and the following results were obtained (weight differences are the average values from two separate test, except for compounds 13 and 17 which are the results from single tests):

$$R^1NH-\overset{\overset{X}{\|}}{C}NH.N=\!\!\!\!\bigcirc\!\!\!\!=N.NHR^2$$

| | X | R¹ | R² | Salt | Weight Difference | | |
|---|---|---|---|---|---|---|---|
| | | | | | 50 ppm. | 25 ppm. | 10 ppm. |
| 1. | O | H | —C(:NH)NH₂ | HCl | 19.1*** | 18.4*** | 14.2*** |
| 2. | O | H | —C(:NH)NHCH₃ | HCl | 21.3*** | 12.9*** | 4.5** |
| 3. | S | H | —C(:NH)NH₂ | — | 18.2*** | 8.6*** | 3.2** |
| 4. | NH | H | —CO.NHCH₃ | HCl | 10.5*** | 10.8*** | 6.1*** |
| 5. | NH | H | —C(:NH)NH.NO₂ | HCl | 13.2*** | 7.5*** | 3.8** |
| 6. | NH | H | —C(:NH)NHN=⟨⟩=NNHC(:NH)NH₂ | — | 10.5*** | 3.0* | 3.0* |
| 7. | NH | H | —CS.NHCH₃ | HCl | 6.6*** | 5.2*** | 3.4* |
| 8. | NH | H | —C(:NH)NHCH₃ | 2HCl | 4.1** | 4.1** | 2.4+ |
| 9. | O | H | —C(N/NH\N-H (imidazoline)) | HCl | 4.5*** | 4.6*** | −1.2NA |
| 10. | NH | H | —C(:NH)NH₂ | 2HNO₃ | 4.8*** | 0.9NA | −0.6NA |
| 11. | NH | H | —C(:NH)NH—⟨⟩ | 2HCl | 3.5** | −1.0NA | 1.1NA |

-continued $$R^1NH-\overset{\overset{X}{\|}}{C}NH.N=\langle\rangle=N.NHR^2$$

| | X | R¹ | R² | Salt | Weight Difference 50 ppm. | 25 ppm. | 10 ppm. |
|---|---|---|---|---|---|---|---|
| 12. | NH | H | −C(=N−CH=CH−NH) (imidazole) | 2HCl | 2.8* | 1.9+ | 2.5* |
| 13. | NH | H | −CO.NH.CH₂−C₆H₅ | HCl | 6.1** | 1.7NA | −1.6NA |
| 14. | O | H | −CO.NH.CH₂−C₆H₅ | HCl | 4.3** | 1.5NA | 2.1+ |
| 15. | NH | H | −CO.NH.CONH₂ (with −C(:NH)NH.N=⟨⟩=N.NH.CONH₂) | HCl | 3.9** | −0.6NA | 0.0NA |
| 16. | NH | H | −CO.NH.CONH₂ | 2HCl | — | 2.3* | −0.7NA |
| 17. | NH | CH₃ | −C(:NH)NH−C₆H₄−Cl, −CO.NHCH₃ | HCl | 5.9** | 0.4NA | −1.1NA |

***significantly different from untreated control at the p <0.001 level
**significantly different from untreated control at the p <0.01 level
*significantly different from untreated control at the p <0.05 level
+significantly different from untreated control at the p <0.1 level
NA not significant

EXAMPLE 9

The procedure described in Example 4 was repeated, using the free base and various salts of N-guanidino-N'-ureido-p-benzoquinonedi-imide and N-guanidino-N'-thioureido-p-benzoquinonedi-imide, and 1-(4-aminoguanidino-phenyl)thiosemicarbazide, and the following results were obtained:

| Compound | Salt | Weight Difference 25 ppm. | 10 ppm. | 5 ppm. |
|---|---|---|---|---|
| NH₂.C(:NH)NHN=⟨⟩=NNHCO.NH₂ | — | 19.2*** | 12.0*** | 6.6*** |
| " | HCl | 18.3*** | 13.4*** | 4.5*** |
| " | HNO₃ | 18.0*** | 9.7*** | 6.0*** |
| " | ½.H₂SO₄ | 16.1*** | 8.1*** | 5.8*** |
| " | CH₃−C₆H₄−SO₃H | 15.3*** | 8.3*** | 1.3NA |
| NH₂.C(:NH)NHN=⟨⟩=N.NH.CS.NH₂ | — | 10.5*** | 2.4* | 1.6NA |
| " | HCl | 6.7*** | 3.5** | 1.9+ |
| " | HNO₃ | 7.9*** | 4.4*** | 2.2* |
| " | CH₃−C₆H₄−SO₃H | 5.8*** | 4.2*** | 2.3* |
| " | ½.H₂SO₃ | 10.2*** | 3.8** | 1.8+ |
| NH₂.C(:NH)NH.NH−⟨⟩−NH.NH.CS.NH₂ | | | | |

***significantly different from untreated control at the p <0.001 level
**significantly different from untreated control at the p <0.01 level
*significantly different from untreated control at the p <0.05 level
+significantly different from untreated control at the p <0.10 level
NA Not significant

EXAMPLE 10

Sixty-four groups of 50 1 day old broiler chicken (32 pens of males and 32 pens of females) were placed in small floor pens bedded with wood shavings and provided with automatic water fountains. The birds in eight randomly chosen such pens four pens of males and four pens of females) were fed on a nutritionally balanced control diet containing no known growth promoter. The remaining seven groups of eight randomly chosen pens four pens of males and four of females) were assigned to the seven diets shown in the table below. The known growth promoters virginiamycin and nitrovin were included as positive controls. At the end of 8 weeks, the groups were weighed and the mean liveweight per bird in each group was determined. The feed conversion ratio (F.C. R. = feed consumed/liveweight) was also determined for each diet.

The following results were obtained:

|  | Dietary Concentration (g/tonne) | Mean, Performance at 8 weeks | | | |
|---|---|---|---|---|---|
|  |  | Growth | | Feed Efficiency | |
|  |  | Mean Live Weight per bird-kg. | % Change from Control | F.C.R. | % Change from Control |
| Control | — | 1.840 | — | 2.094 | — |
| N-Guanidino-N'-ureido-p-benzo-quinonedi-imide hydrochloride | 20 | 1.983*** | +7.8 | 2.104 | +0.5NS |
| " | 10 | 1.978*** | +7.5 | 2.140 | +2.2NS |
| " | 5 | 1.957*** | +6.3 | 2.148 | +2.5NS |
| Virginiamycin | 10 | 1.960*** | +6.5 | 2.139 | +2.1NS |
| " | 5 | 1.972*** | +7.2 | 2.104 | +0.5NS |
| Nitrovin | 10 | 1.934*** | +5.1 | 2.139 | +2.1NS |
| " | 5 | 1.982*** | +7.7 | 2.120 | +1.2NS |

***significantly different from the untreated control at the p <0.001 level
NS not significant.

EXAMPLE 11

One hundred and twelve young pigs, initial weight approximately 35kg. each, were weighed and allocated into eight matched experimental groups of 14 animals each. Each group was randomly assigned to one of eight diets, as specified in the Table below. The diets containing the known growth promoters virginiamycin and nitrovin were included as positive controls. All the animals were fed individually twice daily on an accurately weighed quantity of the diet, according to a feeding scale which was related to body weight and was adjusted weekly. After 25 days and 64 days, the animals were weighed and the mean daily liveweight gain (D.L.W.G.) and food conversion ratio (F.C.R. = kg. food per kg. weight gain) were determined. The following results were obtained:

| Copper | Treatment Growth Promoter | Dietary Inclusion Level g/metric ton. | Mean Performance 25 days | | Mean Performance 64 days | |
|---|---|---|---|---|---|---|
|  |  |  | D.L.W.G.g. | F.C.R. | D.L.W.G.g. | F.C.R. |
| Low | — | — | 701 | 3.317 | 690 | 3.316 |
| Low | Virginiamycin | 10 | 707 | 3.206 | 680 | 3.344 |
| Low | Nitrovin | 10 | 730 | 3.215 | 689 | 3.330 |
| Low | N-Guanidino-N'-ureido-p-benzo-quinonedi-imide hydrochloride | 50/25* | 718 | 3.242 | 697 | 3.276 |
| High+ | — | — | 726 | 3.187 | 702 | 3.209 |
| High | Virginiamycin | 10 | 738 | 3.195 | 698 | 3.288 |
| High | Nitrovin | 10 | 773 | 3.016 | 712 | 3.212 |
| High | N-Guanidino-N'-ureido-p-benzo-quinonedi-imide hydrochloride | 50/25 | 787 | 2.963 | 715 | 3.202 |

*Dietary inclusion level reduced to 25g./tonne on day 21.
+200g. Copper/tonne feed.

EXAMPLE 12

A solution of semicarbazide hydrochloride (72.5g.) in water (325ml.) was added dropwise with stirring to a cooled (10° C.) solution of N-(3-methylguanidino)-p-benzoquinoneimide (57.9g.) in 1N hydrochloric acid (325ml.). The solution was stirred for 4 days at room temperature, and the yellow precipitate was filtered off, washed successively with water and ethanol, and dried in vacuo at 55° C., to give N-(3-methylguanidino)-N'-ureido-p-benzoquinonedi-imide hydrochloride, m.p. 218°-220° C. (decomposition).

The N-(3-methylguanidino)-p-benzoquinoneimide used as starting material in the above process may be prepared as follows:

A solution of 3-methyl-1-aminoguanidine dihydrochloride (60.3g.) in water (190ml.) was added dropwise, over 1 hour, at room temperature to a stirred suspension of p-benzoquinone in ethanol (190ml.). Stirring was continued for 2 hours, and the solution was diluted with water (250ml.), and extracted 3 times with 250ml. portions of ether. The aqueous phase was cooled to 4° C. and treated with concentrated ammonium hydroxide solution (60ml.), and the precipitated solid was filtered off, washed with water, and dried at 55° C. in vacuo, to give N-(3-methylguanidino)-p-benzoquinoneimide, m.p. 215°-216° C. (decomposition).

Similarly, using 4-methylsemicarbazide in place of semicarbazide, there was obtained N-(3-methylguanidino)-N'-(3-methylureido)-p-benzoquinonedi-imide hydrochloride hemihydrate, m.p. 198°-200° C. (decomposition).

EXAMPLE 13

A solution of 1-amino-3-methylguanidine dihydrochloride (1.81g.) in water (5ml.) was added dropwise to a stirred suspension of N-ureido-p-benzoquinoneimide (1.65g.) in methanol (50ml.). The mixture was stirred at room temperature for 2 days, and the yellow solid was filtered off, washed with a little water and then methanol, and dried in vacuo at 55° C., to give N-(3-methylguanidino)-N'-p-benzoquinonedi-imide hydrochloride, m.p. 224°–225° C. (decomposition).

Similarly, using 2-hydrazinoimidazoline dihydrochloride in place of 3-methyl-1-aminoguanidine dihydrochloride, there was thus obtained N-(2-imidazolin-2-ylamino)-N'-ureido-p-benzoquinonedi-imide hydrochloride, m.p. 198° C. (decomposition).

EXAMPLE 14

A solution of 1-aminoguanidine bicarbonate (6.07g.) in glacial acetic acid (40ml.) was added in one portion to a solution of N-(3-methylureido)-p-benzoquinoneimide (4.0g.) in glacial acetic acid (60ml.). The mixture was stirred at room temperature for 18 hours, and the solvent was evaporated, at reduced pressure, below 25° C. The residual oil was treated with concentrated hydrochloric acid (12ml.) and the mixture was diluted with water (60ml.). The precipitated solid was filtered off, washed with water and dried in vacuo at room temperature to give N-guanidino-N'-(3-methylureido)-p-benzoquinonedi-imide hydrochloride monohydrate, m.p. 232°–233° C. (decomposition).

The N-(3-methylureido)-p-benzoquinoneimide used as starting material in the above process may be prepared as follows:

A solution of 4-methylsemicarbazide (2.23g.) in 2N hydrochloric acid (13ml.) was added, over 5 minutes at room temperature, to a vigorously stirred suspension of p-benzoquinone (3.4g.) in water (60ml.) containing two drops of concentrated hydrochloric acid. Stirring was continued for 10 minutes, and the solid which formed was filtered off, washed with water and dried in vacuo at 55° C., to give N-(3-methylureido)-p-benzoquinoneimide, m.p. 180°–182° C. (decomposition).

EXAMPLE 15

A solution of N-guanidino-p-benzoquinoneimide (3.28g.) in 0.5N hydrochloric acid (40ml.) was added at room temperature over 15 minutes to a stirred solution of 1,3-diaminoguanidine hydrochloride (1.26g.) in water (25ml.). The mixture was stirred for 48 hours and allowed to stand for a further 24 hours. To the stirred ice-cold solution was added concentrated ammonium hydroxide solution (10ml.), and after ten minutes, the solid was filtered off, washed with water and dried in vacuo at 60° C., to give 1,3-bis[4-(guanidinoimino)cyclohexa-2,5-dienylideneimino]guanidine trihydrate m.p. 193°–195° C. (decomposition)

EXAMPLE 16

A solution of 1-amino-3-methylguanidine dihydrochloride (1.37g.) in water (5ml.) was added at room temperature to a stirred solution of N-guanidino-p-benzoquinonei-imide (1.64g.) in 0.5N hydrochloric acid (10ml.) containing concentrated hydrochloric acid (1ml.). The solution was stirred for 64 hours at room temperature and diluted with an equal volume of ethanol, and ether was added dropwise, with stirring, to give a yellow precipitate which was filtered off, washed well with ether and dried in vacuo, to give N-guanidino-N'-(3-methylguanidino)-p-benzoquinonedi-imide dihydrochloride monohydrate, m.p. 227°–229° C. (decomposition).

In a similar manner, using 1-amino-3-(4-chlorophenyl)guanidine dihydrochloride in place of 1-amino-3-methylguanidine dihydrochloride, there was obtained an immediate precipitate of N-[3-(4-chlorophenyl)-guanidino]-N'-guanidino-p-benzoquinonedi-imide dihydrochloride, m.p. 260°–261° C. (decomposition).

EXAMPLE 17

A solution of 4-benzylsemicarbazide (1.65g.) in a mixture of 2N hydrochloric acid (15ml.) and ethanol (10ml.) was added to a stirred solution of N-guanidino-p-benzoquinoneimide in 0.5N hydrochloric acid (30ml.). The mixture was stirred for 72 hours at room temperature and the light yellow solid was filtered off, washed with water, and dried in vacuo at 60° C. to give N-(3-benzylureido)-N'-guanidino-p-benzoquinoedi-imide hydrochloride monohydrate m.p. 180°–185° C. (decomposition).

EXAMPLE 18

A solution of 1,3-diaminoguanidine hydrochloride (1.26g.) in water (10ml.) containing concentrated hydrochloric acid (2.5ml.) was added to a stirred solution of N-ureido-p-benzoquinoneimide (3.30g.) in a mixture of methanol (90ml.) and water (10ml.). The solution was stirred for 72 hours at room temperature, and cooled overnight at 4° C., and the solid was filtered off, washed with water and dried in vacuo at 50° C. to give 1,3-bis(4-semicarbazonocyclohexa-2,5-dienylideneimino)guanidine, m.p. 203°–205° C. (decomposition).

EXAMPLE 19

A solution of 1-aminobiuret hydrochloride (1.3g.) in water was added to a solution of N-guanidino-p-benzoquinoneimide (0.82g.) in water containing 2N hydrochloric acid (5ml.). The solution was stirred overnight, and the solid product was filtered off, washed with water, then ethanol, and dried in vacuo at 60° C. to give N-(3-carbamoylureido)-N'-guanidino-p-benzoquinonedi-imide hydrochloride monohydrate m.p. 211° C. (decomposition).

EXAMPLE 20

The process described in Example 1 was repeated, using a similar quantity of N-(3-methylguanidino)-N'-ureido-p-benzoquinonedi-imide, N-guanidino-N'-(4-methylsemicarbazono)-p-benzoquinonedi-imide or 1,3-bis[4-(guanidinoimino)cyclohexa-2,5-dienylimino]guanidine, in place of N-guanidino-N'-ureido-p-benzoquinonedi-imide, to give premixes suitable for dilution with an animal foodstuff.

What we claim is:

1. In the practice of the husbandry of meat-producing, domestic animals, the method for improving the rate of growth of animals or for improving the efficiency of the utilisation of animal foodstuffs which comprises orally administering to said animals a composition containing from 0.0001 to 0.025% w/w of a material selected from quinone derivatives of the formula:

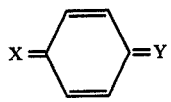

wherein X is guanidinoimino, unsubstituted or bearing one substituent on nitrogen selected from $C_{1-3}$alkyl, and phenyl, unsubstituted or substituted by halogen; or 2-imidazolin-2-ylhydrazono; and Y is guanidinoimino, unsubstituted or substituted as defined above; 3-nitroguanidinoimino; semi-carbazono or thiosemicarbazono unsubstituted or substituted on N-4 by carbamoyl, benzyl, $C_{1-3}$alkyl or alkenyl, or phenyl; 3-[4-(guanidinoimino)cyclohexa-2,5-dienylideneimino]-guanidinoimino; 3-(4-semicarbazonocyclohexa-2,5-dienylideneimino)guanidinoimino; dihydro derivatives thereof; salts thereof; and salts of dihydro derivatives thereof, together with a liquid or solid, edible, non-toxic diluent or carrier.

2. The method of claim 1 which comprises orally administering a composition containing from 0.0001 to 0.005% w/w of N-guanidino-N'-ureido-p-benzoquinonedi-imide, N-(3-methylguanidino)-N'-ureido-p-benzoquinonedi-imide, N-guanidino-N'-thioureido-p-benzoquinonedi-imide, N-guanidino-N'-(3-nitroguanidino)-p-benzoquinonedi-imide or 1,3-bis[4-(guanidinoimino)cyclohexa-2,5-dienylideneimino]-guanidine, or a salt thereof.

3. The method of claim 1 which comprises orally administering a composition containing from 0.0001 to 0.005% w/w of N-guanidino-N'-ureido-p-benzoquinonedi-imide or salt thereof.

* * * * *